(12) United States Patent
Matzenbacher (10) Patent No.: US 10,952,834 B2
(45) Date of Patent: Mar. 23, 2021

(54) DEVICE AND METHOD FOR MITIGATING THE ASCENSION OF TESTICLES DURING CASTRATION OF LIVESTOCK

(71) Applicant: Scott A. Matzenbacher, Ft. Sam Houston, TX (US)

(72) Inventor: Scott A. Matzenbacher, Ft. Sam Houston, TX (US)

(*) Notice: Subject to any disclaimer, the term of this patent is extended or adjusted under 35 U.S.C. 154(b) by 52 days.

(21) Appl. No.: 16/180,533

(22) Filed: Nov. 5, 2018

(65) Prior Publication Data
US 2019/0133735 A1    May 9, 2019

Related U.S. Application Data

(60) Provisional application No. 62/583,102, filed on Nov. 8, 2017.

(51) Int. Cl.
*A61D 1/06*    (2006.01)
*A61B 17/122*   (2006.01)

(52) U.S. Cl.
CPC .............. *A61D 1/06* (2013.01); *A61B 17/122* (2013.01)

(58) Field of Classification Search
CPC ... A61B 17/083; A61B 17/1227; A61B 17/30; A61B 17/122; F16B 2/248; A61D 1/06
See application file for complete search history.

(56) References Cited

U.S. PATENT DOCUMENTS

| | | | |
|---|---|---|---|
| 450,266 A * | 4/1891 | Truax | A61B 17/30 606/210 |
| 1,002,961 A * | 9/1911 | Beuoy | A61B 17/12009 606/135 |
| 2,080,173 A * | 5/1937 | Guimond | A44B 99/00 24/555 |
| 2,845,291 A * | 7/1958 | Priestman | F16B 2/248 403/14 |
| 4,120,301 A * | 10/1978 | Lovick | A61D 1/06 606/135 |
| 4,269,190 A * | 5/1981 | Behney | A61B 17/1227 606/157 |
| 4,444,187 A * | 4/1984 | Perlin | A61B 17/1227 606/158 |
| 4,658,822 A * | 4/1987 | Kees, Jr. | A61B 17/1227 24/546 |
| 9,341,203 B1 * | 5/2016 | Disharoon | F16B 2/248 |
| 2002/0077649 A1 * | 6/2002 | Lasner | A61B 17/30 606/174 |
| 2006/0100646 A1 * | 5/2006 | Hart | A61B 17/1227 606/151 |

* cited by examiner

*Primary Examiner* — Alexander J Orkin
(74) *Attorney, Agent, or Firm* — Black Dog Law, PLLC; Katherine Sullivan (57) ABSTRACT

A device and method for mitigating the frequency of lost testicles during castration by stopping the testicles from ascending into the body. The device includes a compressing pair of elongated members attached to a handle. The method includes applying the device to the spermatic cord above the testicles immediately before castration.

1 Claim, 9 Drawing Sheets

DEVICE AND METHOD FOR MITIGATING THE ASCENSION OF TESTICLES DURING CASTRATION OF LIVESTOCK

CROSS-REFERENCE TO RELATED APPLICATIONS

This application claims priority to U.S. Patent Provisional Application No. 62/583,102, "Method and Device for Holding the Testicles during Castration of Male Calves" filed on Nov. 8, 2017.

FIELD OF THE INVENTION

The present invention relates to castration of male livestock, including but not limited to cattle, sheep or goats. More particularly the present invention relates to a method and instrument to prevent the testicles from ascending up into the body during attempted castration.

BACKGROUND OF THE INVENTION

Young male livestock are the most valued by producers and meat packers when the testicles are removed, through a procedure called castration. There are several different methods of castration.

One difficulty in performing almost any type of castration is having the hands free to carry out the actual process of castration, whether it be via banding, clamping, or surgically. A physical reflex to touch or handling called the cremasteric reflex causes the testicles to be drawn back up towards the main body of the animal making it more difficult to properly carry out an effective castration. The cremasteric reflex occurs when an area near the testicles is touched or disturbed and the cremaster muscles which run vertically along the spermatic cords contract and cause the testicles to draw up closer or even up in to the body cavity.

The testicle may be withdrawn up into the body for multiple days at a time. The potential for missed testicles is high and can be costly.

In elastic band castration, an elastomer tool is used to expand rubber rings, which while expanded, are placed over the testicles and released onto the neck of the scrotum, which houses the spermatic cords and blood supply to the testicles. The rubber band constricts and stops the blood flow to the testicles and after a period of time, the testicles will fall off. The use of elastic band castration is normally performed when the animal is fairly young.

Another method for castration of male livestock is use of the Burdizzo clamp. The Burdizzo clamp is places above the testes on the spermatic cord with the jaws of the Burdizzo clamp being brought together to crush the spermatic cord. While the spermatic cord and vessels are being held by the jaws of the Burdizzo clamp, the cord is rocked back and forth to ensure it is crushed. This procedure is repeated for the spermatic cord of the other testicle.

If surgical castration is being performed on the male animal, it is critical that the testicle be extended down in the scrotum and not withdrawn up into the body of the animal. While the testicles are extended, they are surgically removed with a knife. An emasculator may be used to crush and cut blood vessels in the spermatic cord at the same time. The emasculator lessens the risk of bleeding.

Each of the techniques just described requires that the testicles of the male livestock be retained in the scrotum and prevented from being withdrawn up into the body of the male animal.

In order to prevent the testicles from ascending up into the body, typically one hand is needed to hold the spermatic cord above the testicles themselves. The present device and method disclosed hold and place pressure on the spermatic cords to prevent the testicles from ascending into the body, freeing up the hands of the handler to enable them to perform an effective castration procedure.

It is an object of the present invention to provide an apparatus to mitigate a male livestock from withdrawing testicles up into his body during castration.

It is yet another object of the present invention to provide a spring-loaded device that can be placed above the testicles of a male livestock and compress the spermatic cords and connective tissue during the process of castration to prevent the testicles from being withdrawn up into the male's body.

It is yet another object of the present invention to provide an opposing spring-loaded device where opposing spring jaws can be placed over the spermatic cord of a young male livestock to prevent the testicles from being withdrawn into the body during castration.

It is still another object of the present invention to provide opposing spring-loaded jaws on one end and a handle on the other end, which opposing spring jaws may be placed around the spermatic cord of a young male livestock to prevent withdrawing of the testicles into the male's body during castration.

SUMMARY OF THE INVENTION

The present invention is a device for holding the spermatic cord above the testicles to aid in castration. The invention has a handle portion and two wire members which extend out from the handle portion. The two wire members are the actual means for compressing the spermatic cord to prevent the testicles from being pulled back up into the body by reflex. There are 2 different versions of the invention, and one of the versions has two sizes. In the original version of the invention the wire members bend inwardly and fold back over themselves. In the improved version of the invention the wire members bend upwards and back upon themselves, providing two points of contact for compression of the spermatic cords. There are two different sizes of the invention. One size is for smaller livestock and the second size is for larger or older livestock. In all versions of the invention a rubber tubing is included over the surface of the wire to mitigate skin abrasions as well as to aid in holding the device securely in place.

To use the invention, hold the testicles securely in one hand and apply the compressing members along either side of the spermatic cord.

DETAILED DESCRIPTION OF THE DRAWINGS

Figure 1:
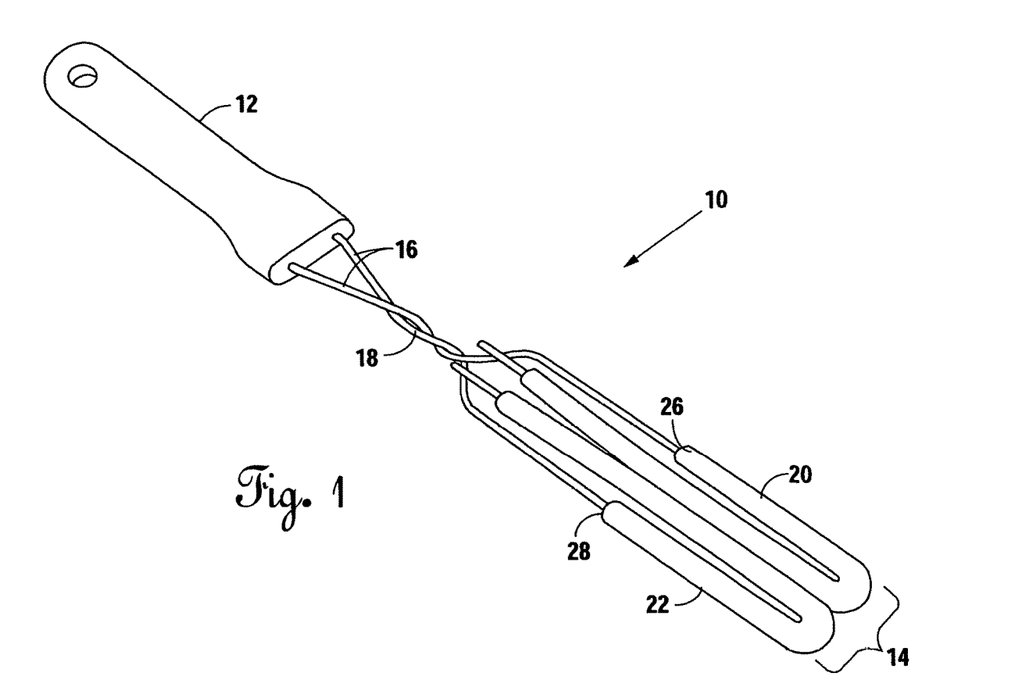
FIG. 1 is a perspective view of an embodiment of the testicle retaining device to be used during castration of young male calf.

FIG. 1 shows a perspective view of a testicle retaining device 10. The testicle retaining device 10 has a handle on one end a clamping wire jaws 14 on the other end thereof.

In one embodiment of the testicle retaining device 10 has two strands of wire 16 twisted together with one end thereof being received inside of handle 12. The opposite end of the wire 16 has a twisted portion 18 and a bent portion to form opposing jaws 20 and 22. On the ends of opposing jaws 20 and 22 is located rubber tubing 26 and 28. In this embodiment the bending of the wire 16, it is important that opposing jaws 20 and 22 be pressing against each other.

Figure 2:
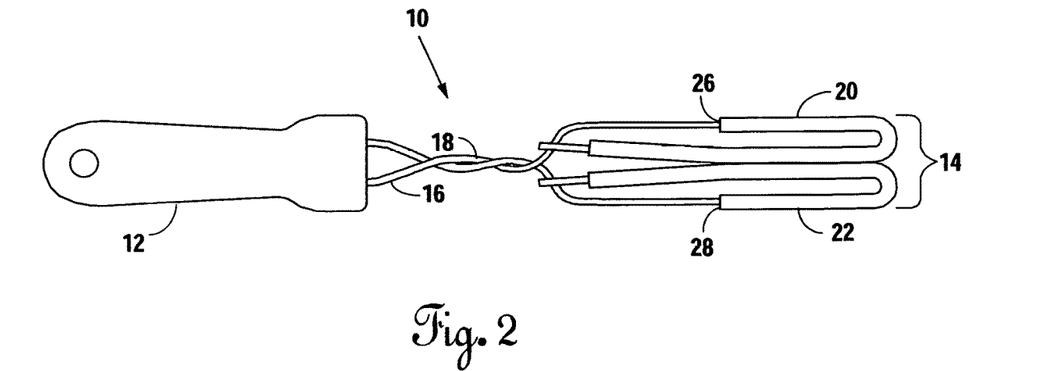
FIG. 2 is a top view of FIG. 1.

FIG. 2 shows a top view of a testicle retaining device 10. This perspective clearly shows the opposing jaws 20 and 22 bending medially towards each other to create the compression.

Figure 3:
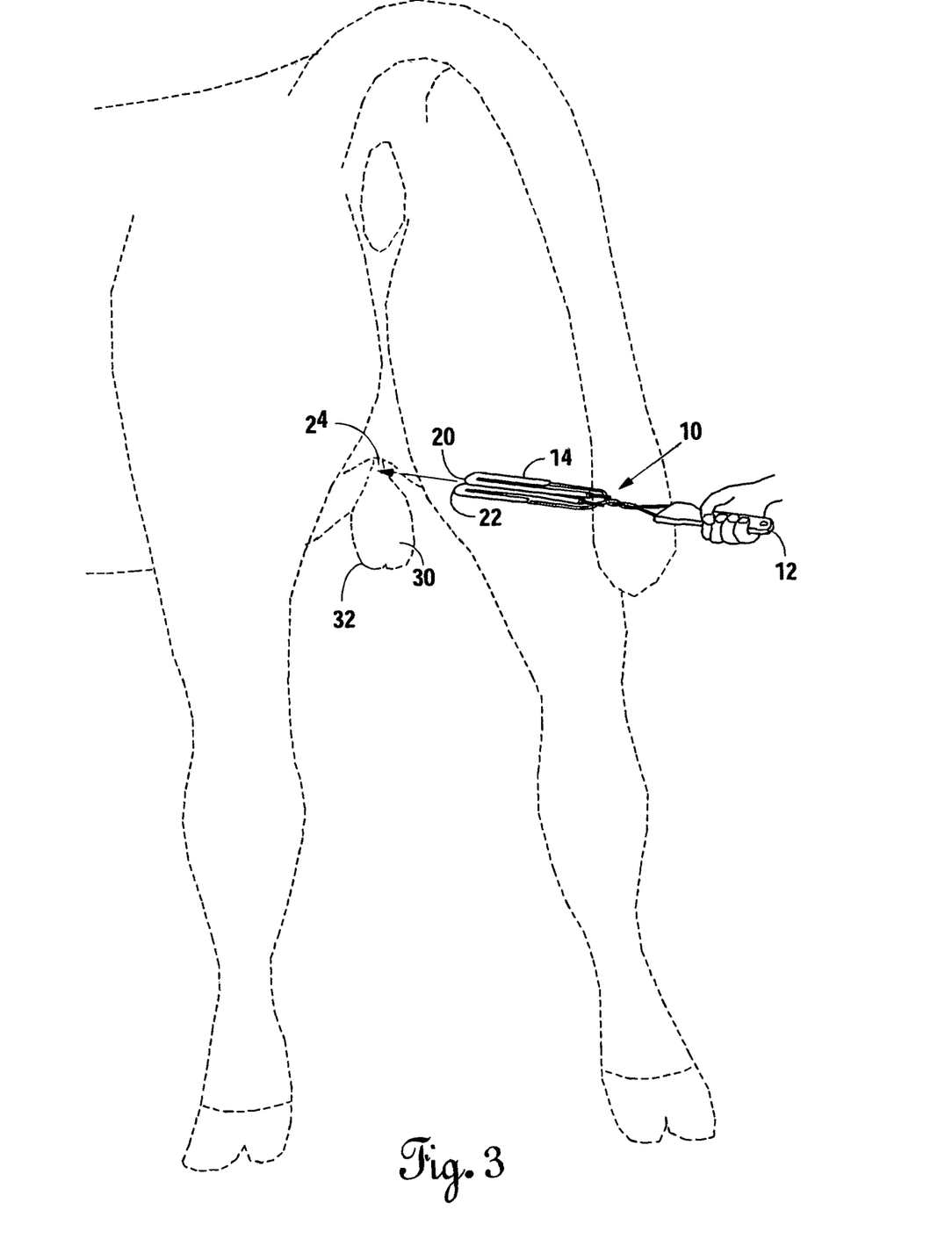
FIG. 3 is an environmental perspective view showing the testicle retaining device being applied to a male calf.
Figure 8:
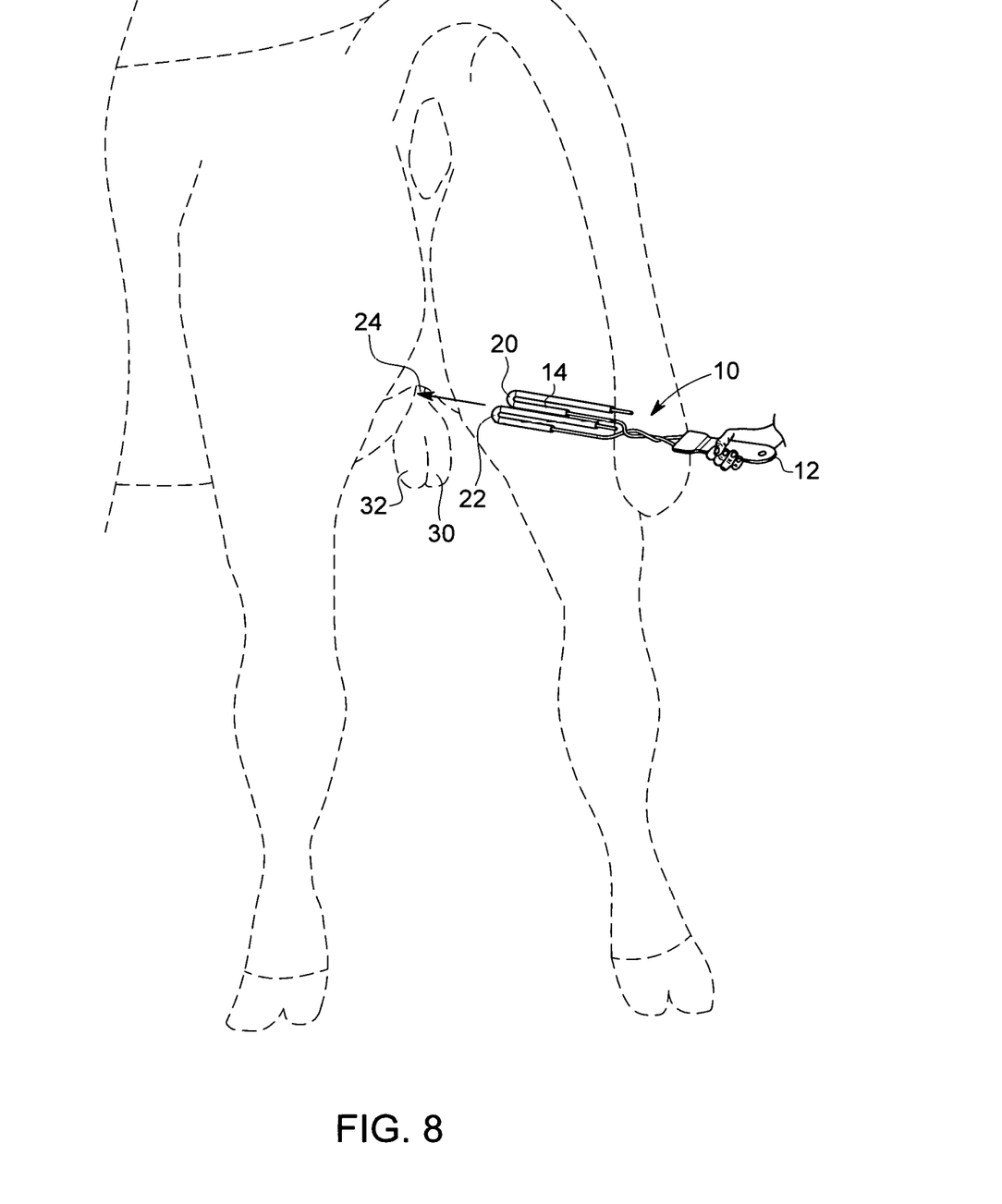
FIG. 8 is an environmental perspective view showing the preferred embodiment of the testicle retaining device being applied to a male calf.

In FIG. 3, for illustration purposes, the young male calf that is about to be castrated is shown in the standing position, which is the position of most young male calves during castration. In actual practice, the young male may be driven into a holding chute during castration. The testicle retaining device 10 is gripped by the handle 12 so that the clamping wire jaws 14 can be pushed against the spermatic cord 24 in the area above the testicles 30 on the young bull calf being castrated. The clamping wire jaws 14 were spread apart enough to receive the spermatic cord 24 therein. The closing force of the opposing jaws 20 and 22 of the testicle retaining device 10 puts enough pressure so that the young male calf cannot withdraw his testicles 30 up into the body. FIG. 8 shows the preferred embodiment of the device in the same view for illustration purposes.

Figure 4:
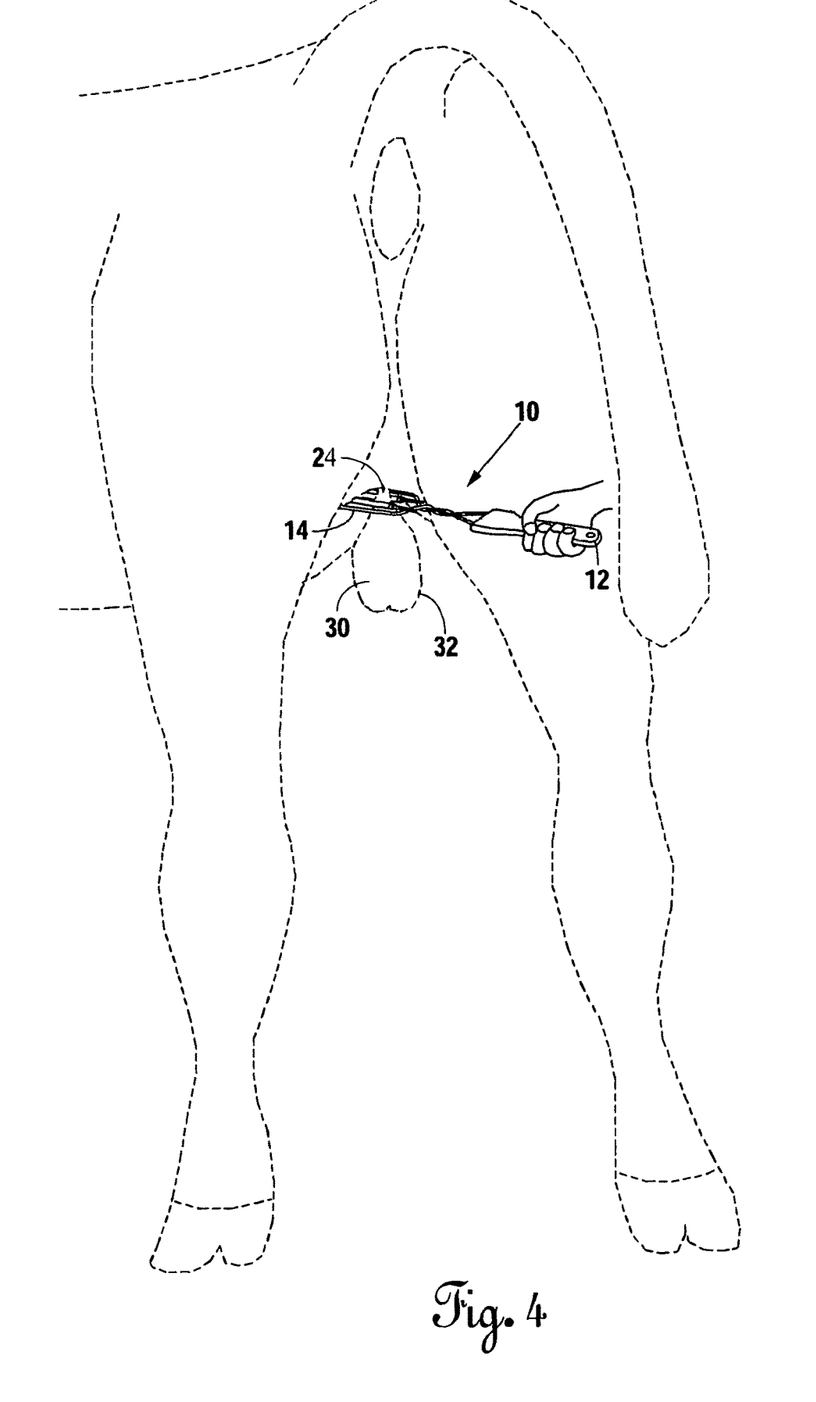
FIG. 4 is an environmental view showing the testicle retaining device in place.
Figure 9:
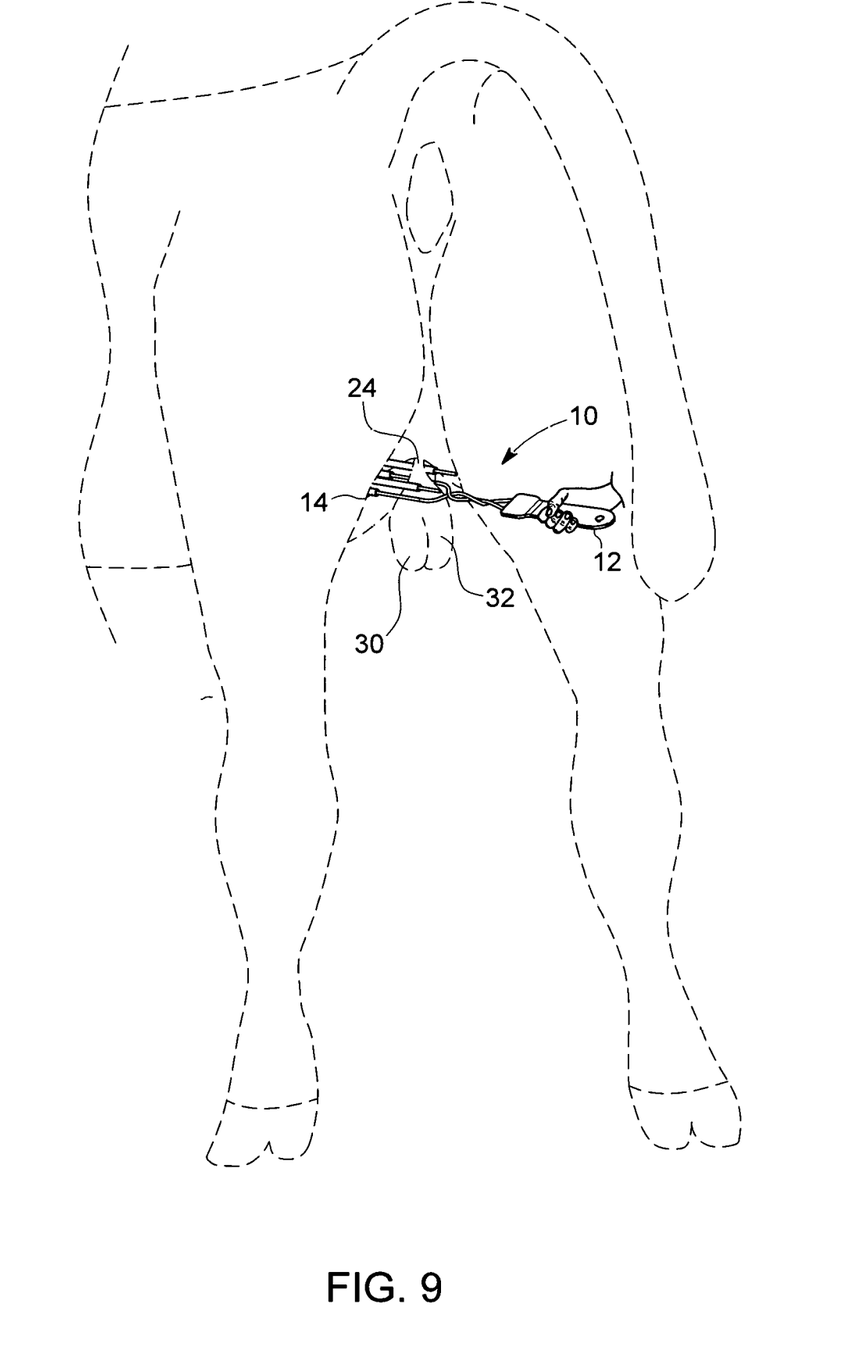
FIG. 9 is an environmental view showing the preferred embodiment of the testicle retaining device in place.

Referring to FIGS. 4 and 9, the testicle retaining device 10 is in place with the clamping wire jaws 14 being secured on the spermatic cord 24 above the scrotum 32 containing the testicles 30. This mitigates the bull calf from withdrawing his testicles 30 up into his body. FIG. 9 is an illustration using the preferred embodiment of the invention.

Figure 5:
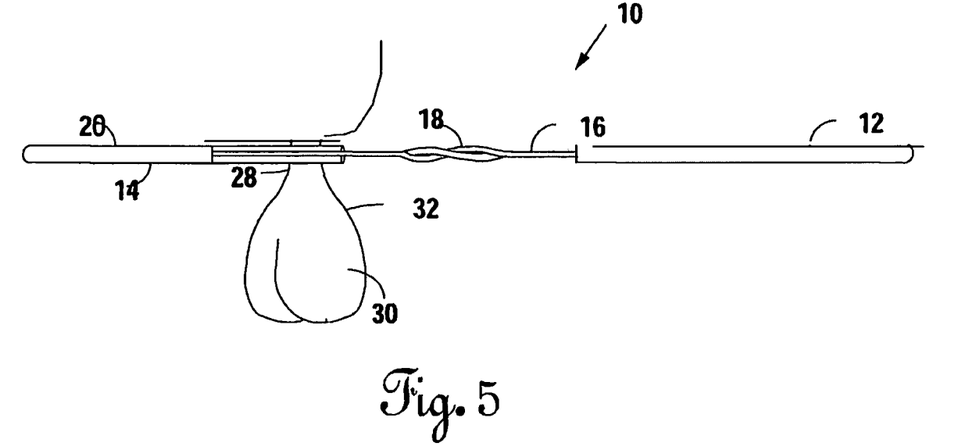
FIG. 5 is a partial side view of a male calf showing the testicle retaining device as applied to the spermatic cord above the testicles contained in the scrotum.

Referring to FIG. 5, the testicle retaining device 10 is in place with the clamping wire jaws 14 being secured on the spermatic cord above the testicles 30 as contained in the scrotum 32. The rubber tubing 26 and 28 (not shown) mitigates the wire 16 from hurting or cutting the bull calf and also aids in holding the device in place on the spermatic cord.

Figure 6:
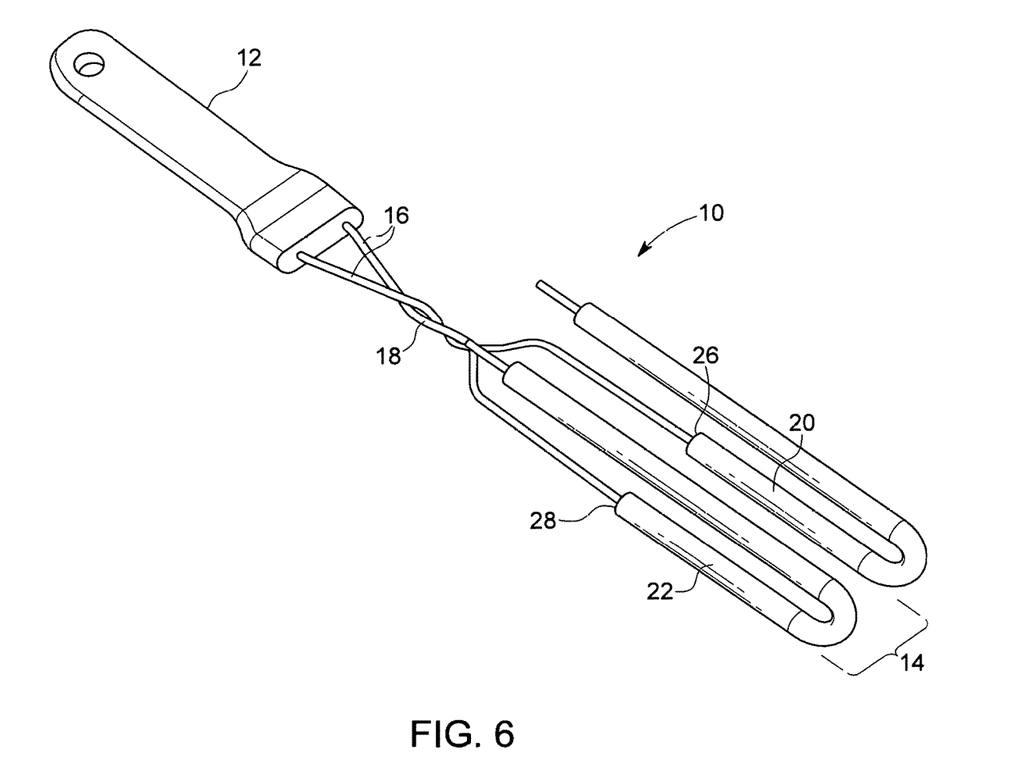
FIG. 6 is a perspective view of the preferred embodiment of the testicle retaining device.

FIG. 6 is a perspective view of the preferred embodiment of the testicle retaining device. Here the opposing jaws 20 and 22, are bent 14 superiorly and back towards the handle 12.

Figure 7:
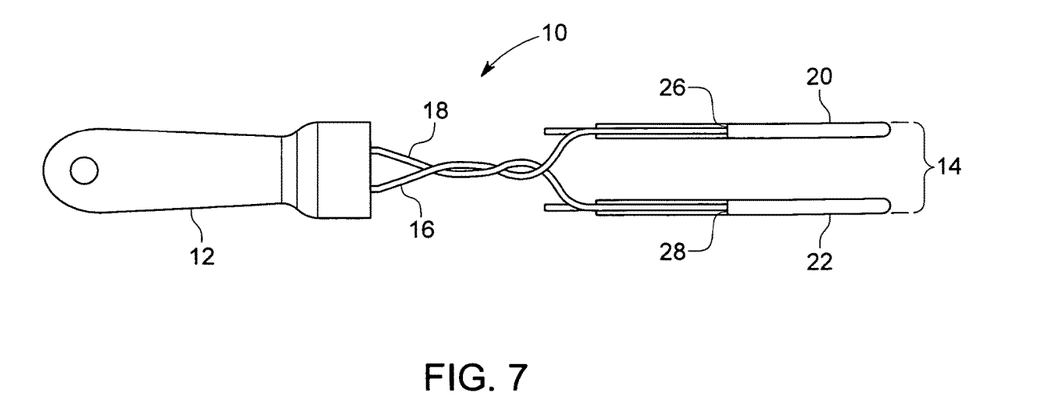
FIG. 7 is a bottom view of FIG. 6.

FIG. 7 is a bottom view of the preferred embodiment of the testicle retaining device.

Figure 10:
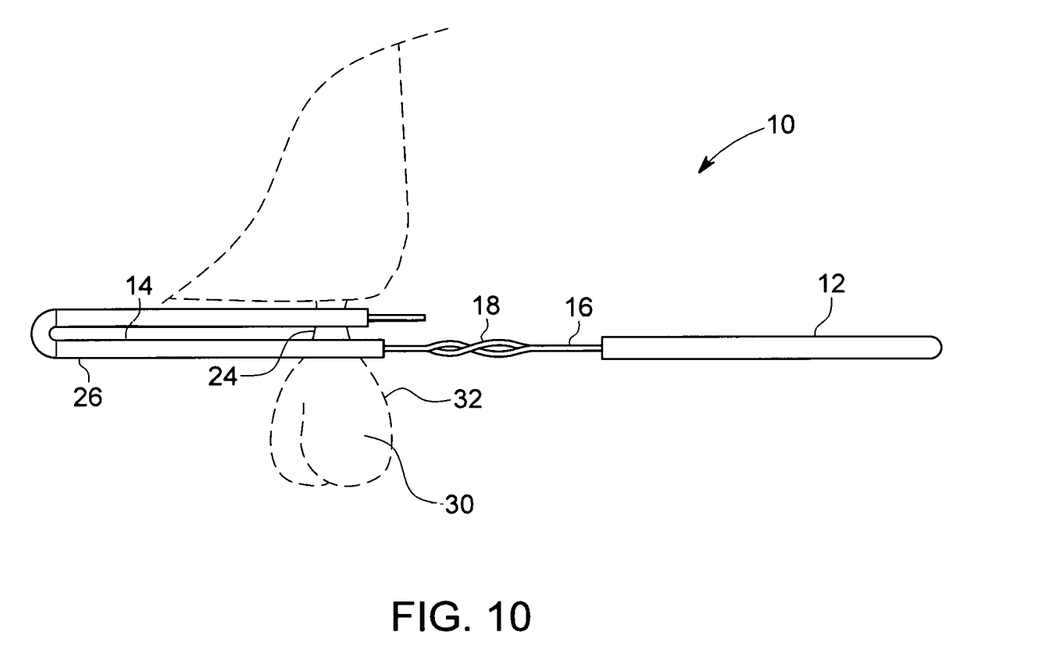
FIG. 10 is a partial side view of a male calf showing the preferred embodiment of the testicle retaining device as applied to the spermatic cord above the testicles contained in the scrotum.

Referring to FIG. 10, the preferred embodiment of the testicle retaining device is in place with the compressing wire jaws 14 being secured on the spermatic cord above the testicles 30 as contained in the scrotum 32. The rubber tubing 26 and 28 (not shown) mitigates the wire 16 from hurting or cutting the bull calf and also aids in holding the device in place on the spermatic cord.

Figure 11:
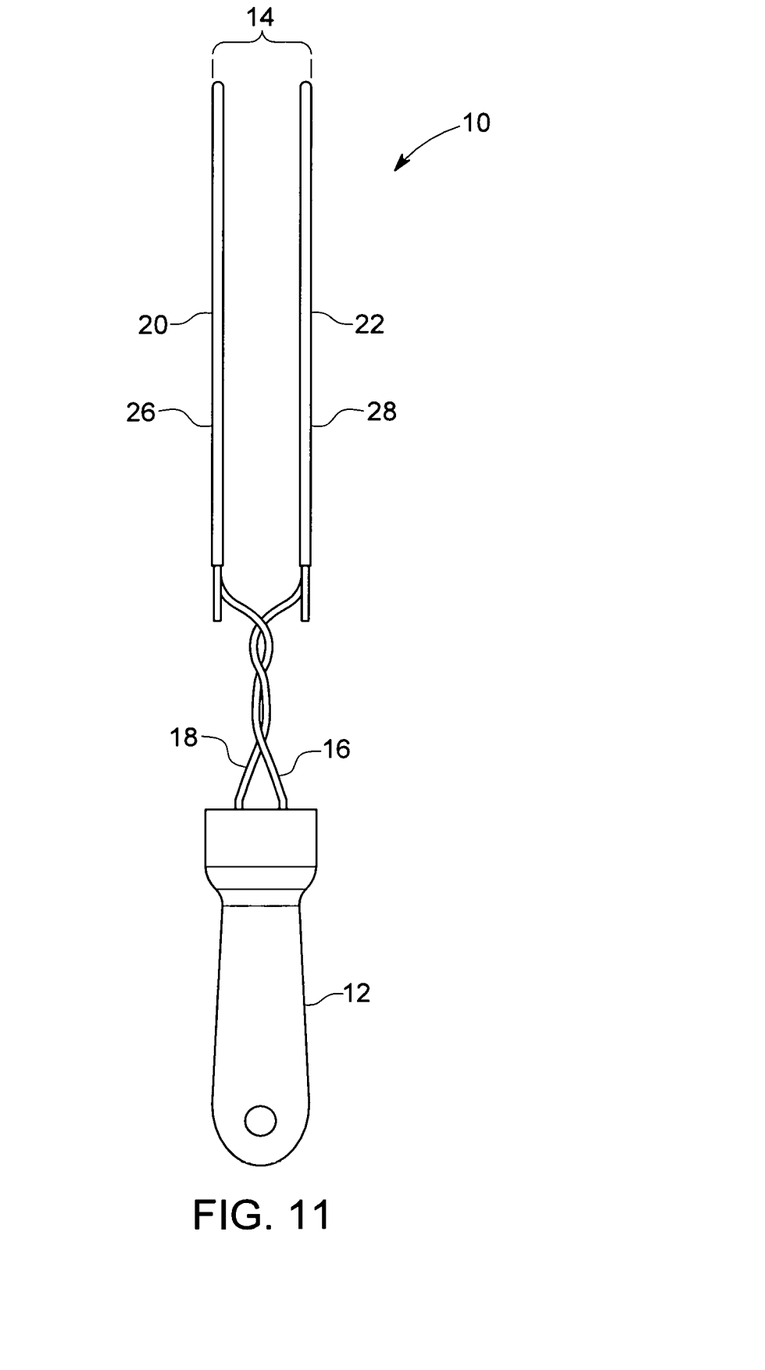
FIG. 11 is a top view of the preferred embodiment of the testicle retaining device.

FIG. 11 is a top view of the preferred embodiment of the testicle retaining device. The two wires 20 and 22 bend superiorly 14 and fold back towards the handle 12.

The use of the testicle retaining device 10, as shown and explained in connection with FIGS. 1-5, one individual can place the testicle retaining device 10 in position and thereafter perform the castration. This is especially true by use of elastic band that obstructs blood flow to the testicles 30 and scrotum 32. By the use of the testicle retaining device 10, the problem of testicles 30 being drawn up into the body of the calf during castration is eliminated.

DETAILED DESCRIPTION OF THE INVENTION

The device has two main portions: the handle and the compressing members. The handle is made of a solvent proof plastic-like material. The compressing members for holding the spermatic cord are made of a metal wire where part of the wire is surrounded by a rubber tubing. The rubber tubing is to mitigate skin abrasions during application of the device to the spermatic cord. The two wire members extend out from the handle portion separately and then twist around each other 1-2 times before extending out separately again. The two wire members then extend out and then fold back upon themselves.

One embodiment of the device which is shown in FIGS. 1-5 shows the device where the wire members bend medially towards the other member and fold back upon themselves.

The preferred embodiment is an improvement upon the original device. The preferred embodiment is shown in FIGS. 6-11 shows the device where the each of the wire members bend superiorly to then fold back upon themselves. This creates an additional point of compression along the spermatic cord. This embodiment also has two different sizes. One size for livestock between 200 and 600 pounds and a second size for livestock between 500 and 800 pounds. The difference in sizing being that the two compressing members are a greater distance apart for the 500-800 lb livestock to accommodate for a larger spermatic cord. For the smaller size the compressing members are spaced ½ inch apart. For the larger size the wire members are spaced one inch apart. The two wire members compress the spermatic cord. The compressing force is created by the close proximity of the two wire members when the members are pressed over the spermatic cord. Once the device is in place, one can continue with the decided upon banding or castration procedure.

What is claimed is:

1. A method comprising:
   receiving an animal having a spermatic cord extending from a body of the animal to at least one testicle;
   selecting a testicle retaining device having a handle; and
   a clamping jaw comprising a first end, a second end, a twisted region, a first strand, and a second strand, the first end fastened to the handle, the twisted region extending from the first end and having the first strand and the second strand twisted, the first strand and the second strand extending from the twisted region in a first direction to form a first region, and a second region extending from the first region in a second direction, the second direction being opposite the first direction;
   a first rubber portion extending around the first strand and a second rubber portion extending around the second strand wherein the first strand and the second strand extend substantially parallel within the first region; and spreading apart the first and second strands, receiving the spermatic cord between the first rubber portion and the second rubber portion, and clamping the testicle retaining device onto the spermatic cord between the first rubber portion and the second rubber portion to mitigate the animal from withdrawing the at least one testicle into the body.

\* \* \* \* \*